United States Patent [19]

Sestanj

[11] 4,254,109

[45] Mar. 3, 1981

[54] 1H-BENZ[de]ISOQUINOLINE-2(3H)-ACETIC ACID DERIVATIVES

[75] Inventor: Kazimir Sestanj, St. Laurent, Canada

[73] Assignee: Ayerst, McKenna & Harrison Inc., Montreal, Canada

[21] Appl. No.: 92,604

[22] Filed: Nov. 8, 1979

[51] Int. Cl.$^3$ .................... C07D 221/14; A61K 31/47
[52] U.S. Cl. .................................. 424/178; 424/258; 546/98
[58] Field of Search .................. 546/98; 424/178, 258

[56] References Cited

U.S. PATENT DOCUMENTS 3,821,383  6/1974  Sestanj et al. .................... 424/258

4,118,495  10/1978  Lippman .......................... 424/258

OTHER PUBLICATIONS

Dvornik, Science 182, 1146 (1973).
Noguchi et al. C.A. 72, 56708r (1970).
Graushen et al. J. Het. Chem 11, 33 (1974).
Shirosaki, Chem. Abs. 86, 89467d (1977).

Primary Examiner—Mark L. Berch
Attorney, Agent, or Firm—Arthur E. Wilfond

[57] ABSTRACT

Herein disclosed are 6-substituted derivatives of 1,3-dioxo-1H-benz[de]isoquinoline-2(3H)-acetic acid. The derivatives inhibit lens aldose reductase.

9 Claims, No Drawings

1H-BENZ[de]ISOQUINOLINE-2(3H)-ACETIC ACID DERIVATIVES

RELATED APPLICATION

A related application is K. Sestanj, U.S. Pat. application No. (92,397), filed on the same day as this application.

BACKGROUND OF THE INVENTION

This invention relates to 1H-benz[de]isoquinoline-2(3H)-acetic acid derivatives, therapeutically acceptable salts thereof, a process for their preparation and to pharmaceutical compositions thereof. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy and cataracts. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase (see D. Dvornik et al., Science, 182, 1146 (1973) and useful for the treatment of diabetic complications such as diabetic cataracts, neuropathy, nephropathy and retinopathy (see K. Sestanj, N. Simard-Duquesne and D. M. Dvornik, U.S. Pat. No. 3,821,383, June 28, 1974). This compound also stimulates insulin secretion and prevents or decreases the secretion of excessive amounts of glucagon, see W. Lippmann, U.S. Pat. No. 4,118,495, Oct. 3, 1978. Consequently, this compound represents an important adjunct to the treatment of diabetes mellitus. U.S. Pat. No. 3,821,383 also discloses the 5-nitro, 5-amino and 6-bromo derivatives of 1,3-dioxo-1H-benz[de]isoquinoline-2(3H)-acetic acid. T. Noguchi et al, Chem. Abstr., 72, 56708r (1970) for Japanese Pat. No. 69/18,955, Aug. 18, 1969 discloses, amongst other things, the 6-methoxy derivative of 1,3-dioxo-1H-benz[de]isoquinoline-2(3H)-acetic acid as a fluorescent whitening agent for fibers.

The present application discloses a new group of 1H-benz[de]isoquinoline compounds which inhibit aldose reductase in the diabetic subject. Some of these compounds beneficially effect the secretions of insulin and glucagon in the diabetic, and also inhibit gastric acid secretion.

SUMMARY OF THE INVENTION

The compounds of this invention are represented by formula I

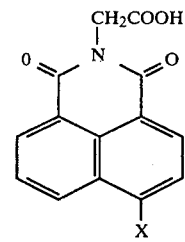

in which X is selected from the group consisting of benzoyl, chloro, phenylthio, (2-carboxyphenyl)thio or decylthio; or a therapeutically acceptable salt thereof with an organic or inorganic base.

The compounds of formula I are prepared by a process described hereinafter.

A method is provided for preventing or relieving diabetes mellitus associated complications in a diabetic mammal by administering to said mammal an alleviating or prophylactic amount of the compound of formula I or a therapeutically acceptable salt thereof.

Compounds of formula I, or a therapeutically acceptable salt thereof with organic or inorganic base, when admixed with a pharmaceutically acceptable carrier, form a pharmaceutical composition which can be used according to the preceding method.

DETAILED DESCRIPTION OF THE INVENTION

The "lower alkyl" as used herein means straight chain alkyl radicals containing from one to four carbon atoms and branched chain alkyl radicals containing three or four carbon atoms and includes methyl, ethyl, propyl, isopropyl, butyl, isobutyl and tertiary butyl.

The compounds of formula I form salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amounts of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6 containing a pharmaceutically acceptable buffer.

The dosage of the present therapeutic agents will vary with the form administration and the particular compound chosen. Furthermore, it will vary with the particular host under treatment. Generally, treatment is initiated with small dosages substantially less than the optimal dose of the compound. Thereafter, the dosage is increased by small increments until the optimal effect under the circumstances is reached. In general, the compounds of this invention are most desirably administered at a concentration level that will generally afford effective results without causing any harmful or deleterious side effects. For topical administration a 0.05–0.2% solution may be administered dropwise to the eye. The frequency of installation varies with the subject under treatment from a drop every two or three days to once daily. For oral or parenteral administration a preferred level of dosage ranges from about 0.1 mg to about 200 mg per kilo of body weight per day, although aforementioned variations will occur. However, a dosage level that is in the range of from about 3.0 mg to about 30 mg per kilo of body weight per day is most satisfactory.

Unit dosage forms such as capsules, tablets, pills and the like may contain from about 5.0 mg to about 50 mg of the active ingredients of this invention, dependent on the type of unit dosage, preferably with a significant quantity of a pharmaceutical carrier. Thus, for oral administration, capsules can contain from between about 5.0 mg to about 50 mg of the active ingredients of this invention with or without a pharmaceutical diluent. Tablets, either effervescent or noneffervescent, can contain between about 5.0 to 50 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents, for example, maize starch and alginic acid and lubricating agents for example, magnesium stearate.

Syrups or elixirs suitable for oral administration can be prepared from water soluble salts, for example, sodium 1,3-dioxo-6-(phenylthio)-1H-benz[de]-isoquinoline-2(3H)-acetate, and may advantageously contain glycerol and ethyl alcohol as solvents or preservatives.

The compound of formula I, or a therapeutically acceptable salt thereof, also can be used in combination with insulin or oral hypoglycemic agents to produce beneficial effect in the treatment of diabetes mellitus. In this instance, commercially available insulin preparations or oral hypolycemic agents, exemplified by acetohexamide, chlorpropamide, tolazamide, tolbutamide and phenformin, are suitable. The compound of formula I, or a therapeutically acceptable salt thereof, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 32 ed., Medical Economics Co., Oradell, N.J., U.S.A. 1978. When used in combination, the compound of formula I, or its therapeutically acceptable salt, is administered as described previously. The compound of formula I, or its therapeutically acceptable salt, can be administered with the oral hypoglycemic agent in the form of a pharmaceutical composition comprising effective amounts of each agent.

The aldose reductase inhibiting effects of the benzisoquinoline acetic acid derivatives of formula I and their pharmaceutically acceptable salts with an organic or inorganic base may be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the compounds of this invention were evaluated in the above in vitro test (the results for 1,3-dioxo-1H-benz[de]isoquinoline-2(3H)-acetic acid, see U.S. Pat. No. 3,821,383 cited hereinbefore, also is included for comparative purposes):

| Compound | Percent Inhibition at Different Molar Concentrations (in vitro) | | |
|---|---|---|---|
| | $10^{-5}$ | $10^{-6}$ | $10^{-7}$ |
| Compound of Formula I in which X = benzoyl (product of Example 1) | 85 | 65 | 22 |
| Compound of Formula I in which X = chloro (product of Example 2) | 86 | 42 | 9 |
| Compound of Formula I in which X = phenylthio (product of Example 3) | 92 | 71 | 22 |
| Compound of Formula I in which X = (2-carboxyphenyl)thio (product of Example 4) | 91 | 61 | 17 |
| Compound of Formula I in which X = decylthio (product of Example 5) | 60 | 33 | 26 |
| 1,3-Dioxo-1H-benz[de] isoquinoline-2(3H)-acetic acid (U.S. Pat. No. 3,821,383) | 74 | 32 | 5 |

PROCESS OF PREPARATION

The compounds of this invention are prepared by a process involving the condensation of an appropriately substituted 1,8-naphthalic acid anhydride with glycine. This condensation is effected readily by reacting the apropriately substituted naphthalic anhydride with 1.0 to 1.2 molar equivalents of glycine in the presence of 1.0 to 1.2 molar equivalents of a suitable proton acceptor; for example, sodium hydroxide, potassium carbonate or triethylamine. The condensation preferably is done in an inert solvent, for example, water, dimethylformamide or toluene at temperatures ranging from about 100° to 200° C. and reaction times ranging from 15 minutes to six hours. In a preferred and most convenient embodiment of this process, the proton acceptor is sodium or potassium hydroxide and the inert solvent is water.

The appropriately substituted 1,8-naphthalic acid anhydrides are known or can be prepared by known reactions. For example, references describing 4-benzoyl-1,8-naphthalic acid anhydride and 4-chloro-1,8-naphthalic acid anhydride are cited in the examples of this application. The preparation of 4-phenylthio-1,8-naphthalic acid anhydride from 4-chloro-1,8-naphthalic acid anhydride and thiophenol is accomplished by employing the procedure of P. H. Grayshan et al., J. Heterocyclics, 11, 33 (1974) for preparing 4-(2-aminophenylthio)-1,8-naphthalic acid anhydride. By replacing thiophenol with 2-mercaptobenzoic acid or 1-decanethiol in the latter procedure, 4-[(2-carboxyphenyl)thio]-1,8-naphthalic acid anhydride and 4-(decylthio)-naphthalic acid anhydride are obtained, respectively.

Alternatively, the compounds of formula I in which X is phenylthio, (2-carboxyphenyl)thio or decylthio are prepared by reacting the 6-chloro-1,3-dioxo-1H-benzo[de]isoquinoline-2(3H)-acetic acid, or 6-bromo-1,3-dioxo-1H-benz[de]-isoquinoline-2(3H)-acetic acid, with thiophenol, 2-mercaptobenzoic acid and 1-decanethiol, respectively, in the presence of a proton acceptor, preferably an alkali metal carbonate such as potassium carbonate or sodium carbonate. An inert solvent, for example, dimethyl formamide, dioxane or 1,2-dimethoxyethane, is employed. Usually it is most convenient and practical to do this reaction under anhydrous conditions at temperatures ranging from 80°–160° C. and reaction times ranging from 15 minutes to six hours.

The following examples further illustrate this invention.

EXAMPLE 1

6-Benzoyl-1,3-dioxo-1H-benz[de]isoquinoline-2(3H)-acetic acid (I; X=benzoyl)

4-Benzoyl-1,8-naphthalic acid anhydride [2.0 g, 6.6 mmoles, described by K. Dziewonski and M. Rychilk, Chem. Ber., 58, 2239 (1925)], was suspended in 7.9 ml of aqueous 1 N sodium hydroxide containing glycine (0.59 g, 7.9 mmole). The mixture was stirred and heated at reflux for 3 hr. After cooling the mixture was rendered acidic (pH about 2) with 1 N hydrochloric acid. The resulting precipitate was collected, dried and crystallized from glacial acetic acid to give 2.0 g (84% yield) of the title compound, The pure title compound has mp 310°–312° C.; UV (MeOH) 234 and 336 nm, $\epsilon$=43,445 and 15,200, respectively; IR (CDCl$_3$) 2900, 1660, 1695, 1720 cm$^{-1}$; NMR (CDCl$_3$) δ4.8 (s, 2H), 8.0 (m, 10H) and 12.9 (broad, 1H); Anal. Calc'd: C, 7019%; H, 3.65%; N, 3.42%; Found: C, 69.56%; H, 3.70%; N, 3.47%.

EXAMPLE 2

6-Chloro-1,3-dioxo-1H-benz[de]isoquinoline-2(3H)-acetic acid (I; X=Cl)

The title compound (mp 260° C.; UV (MeOH) 235, 339 and 352 nm, $\epsilon$=41,310, 15,190 and 13,700 respectively; IR (CDCl$_3$) 1725, 1705 and 1670 cm$^{-1}$; NMR (DMSO-d$_6$) δ4.6 (s, 2H), 6.0 (m, 1H), 7.9 (m, 2H), 8.45 (m, 3H); Anal. Calc'd: C, 58.05%; H, 2.78%; Found: C, 58.16%; H, 2.74%; N, 4.69%) was obtained in a 75% yield by following the procedure of Example 1 but replacing 4-benzoyl-1,8-naphthalic acid anhydride with an equivalent amount of commercially available 4-chloro-1,8-naphthalic acid anhydride, e.g. see "Catalog Handbook of Fine Chemicals", 1979–1980, Aldrich Chemical Co., Inc., Milwaukee, Wis., U.S.A., changing the reaction time to one hour and recrystallizing the crude precipitated product from anhydrous ethanol.

EXAMPLE 3

1,3-Dioxo-6-(phenylthio)-1H-benz[de]isoquinoline-2(3H)-acetic acid (I; X=SPh)

A mixture of 6-chloro-1,3-dioxo-1H-benz[de]isoquinoline-2(3H)-acetic acid (15.0 g, 52 mmoles), described in Example 2, anhydrous potassium carbonate (7.16 g, 52 mmoles), thiophenol (6.28 g, 5.9 ml, 57 mmoles) and distilled dimethylformamide (250 ml) were heated at reflux for one hr. An additional amount (0.6 g) of thiophenol was added and the mixture was heated at reflux for 0.5 hr. At this point an additional amount (0.7 g) of anhydrous potassium carbonate was added and the mixture heated at reflux for another 0.5 hr. The mixture now was poured into water (1 liter). The aqueous mixture was cooled in an ice bath and rendered acidic with conc hydrochloric acid (15 ml).

The yellow precipitate was collected, washed with water and then diethyl ether and dried. Recrystallization of the precipitate from glacial acetic acid gave 15.0 g of the title compound; mp 250°–253° C.; UV (MeOH) 232, 250 and 345 nm; $\epsilon = 25,800, 19,625$ and $7,340$, respectively; IR (CHCl$_3$) 3000, 1740, 1690, 1648 cm$^{-1}$; NMR (DMSO-d$_6$) $\delta$ 4.66 (s, 2H), 7.45 (s, 5H), 7.25 (d, 1H), 7.86 (d, 1H), 8.4 (m, 3H); Anal. Calc'd: C, 66.11%; H, 3.61%; N, 3.86%; Found: C, 66.26%; H, 3.70%; N, 3.69%.

EXAMPLE 4

1,3-Dioxo-6-[(2-carboxyphenyl)thio]-1H-benz[de]isoquinoline-2(3H)-acetic acid [I; X=

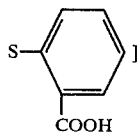

]

A mixture of 6-chloro-1,3-dioxo-1H-benz[de]isoquinoline-2(3H)-acetic acid (10.0 g, 34.5 mmoles, described in Example 2); 2-mercaptobenzoic acid (5.85 g, 37.9 mmoles) and anhydrous potassium carbonate (9.54 g, 37.9 mmoles) in dimethylformamide (300 ml) was heated at reflux for 3 hr. The product in the form of its sodium salt was precipitated from the reaction mixture. The precipitate was collected by filtration and dissolved in water. The solution of the sodium salt was rendered acidic with 2 N hydrochloric acid. The resulting precipitate was collected, dried and crystallized from dimethylformamide and water to give 9.0 g of the title compound; mp 339°–341° C.; UV (MeOH) 231, 254, 336 and 346, $\epsilon = 31,450, 15,810, 8,760$ and $9,210$, respectively; IR (CHCl$_3$) 2900, 1725, 1710, 1675 cm$^{-1}$; NMR (CDCl$_3$) $\delta$ 4.7 (s, 2H), 6.5–8.6 (m, 9H), 13.0 (broad, 1H); Anal. Calc'd: C, 61.91%; H, 3.22%; N, 3.44%; Found: C, 61.51%; H, 3.21%; N, 3.73%.

EXAMPLE 5

1,3-Dioxo-6-(decylthio)-1H-benz[de]isoquinoline-2(3H)-acetic acid (I; X=S-(CH$_2$)$_9$-CH$_3$)

In a nitrogen atmosphere, a suspension of 6-chloro-1,3-dioxo-1H-benz[de]-isoquinoline-2(3H)-acetic acid (5.0 g, 17.3 mmoles, described in Example 2), 1-decanethiol (3.3 g, 3.9 ml, 19 mmoles) and anhydrous sodium carbonate (2.4 g, 17.3 mmoles) in dimethylformamide (150 ml) was stirred and heated at reflux for 15 minutes. After cooling the precipitate was collected by filtration and then dissolved in water. The solution was acidified with 2 N hydrochloric acid and extracted with ethyl acetate. The extract was dried (MgSO$_4$) and evaporated to dryness the oily residue was triturated with hexane. The solid was recrystallized from benzene-hexane to give 4.50 g of the title product; mp 137°–140° C.; UV (MeOH) 257, 329, 343 and 382, $\epsilon = 16,375, 2,849, 4,929$ and $15,820$, respectively; IR (CHCl$_3$) $\delta$2900, 1725 (inflection), 1698, 1662 cm$^{-1}$; NMR (CDCl$_3$) 0.85 (t, 3H, J=5), 1.25 (m, 16H), 3.1 (t, 2H, J=6.5), 4.92 (s, 2H), 8.45 (m, 3H), 9.75 (broad, 1H); Anal. Calc'd: C, 67.42%; H, 6.84%; N, 3.28%; Found: C, 67.17%; H, 6.84%; N, 3.21%.

We claim:

1. A compound of the formula

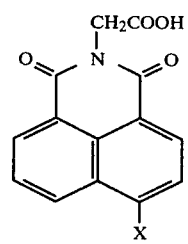

in which X is selected from the group consisting of benzoyl, phenylthio, (2-carboxyphenyl)thio or decylthio; or a therapeutically acceptable salt thereof with an organic or inorganic base.

2. 6-Benzoyl-1,3-dioxo-1H-benz[de]isoquinoline-2(3H)-acetic acid, as claimed in claim 1.

3. 1,3-Dioxo-6-(decylthio)-1H-benz[de]isoquinoline-2(3H)-acetic acid, as claimed in claim 1.

4. 1,3-Dioxo-6-(phenylthio)-1H-benz[de]isoquinoline-2(3H)-acetic acid, as claimed in claim 1.

5. 1,3-Dioxo-6-[(2-carboxyphenyl)thio]-1H-benz[de]isoquinoline-2(3H)-acetic acid, as claimed in claim 1.

6. A pharmaceutical composition, for preventing or relieving diabetic complications consisting of cataracts, neuropathy, nephropathy and retinopathy in a diabetic mammal, which comprises an effective amount of compound of claim 1 or a pharmaceutically acceptable salt thereof with an organic or inorganic base, and a pharmaceutically acceptable carrier.

7. The pharmaceutical composition of claim 6 which also comprises an oral hypoglycemic agent selected from the group consisting of a cetohexamide, chlorpropamide, tolazamide, tolbutamide and phenformin.

8. A method of preventing or relieving diabetic complications consisting of cataracts, neuropathy, nephropathy and retinopathy in a diabetic mammal which comprises administering to said mammal an alleviating or prophylactic amount of a compound of claim 1, or a therapeutically acceptable salt thereof with an organic or inorganic base.

9. The method of claim 8 in which the administration claim 1 is performed simultaneously or sequentially with the adminstration of an effective blood glucose lowering amount of insulin or an oral hypoglycemic agent selected from the group consisting of acetohexamide, chloropropamide, tolazamide, tolbutamide nd phenformin.

* * * * *